(12) United States Patent  
Kreft

(10) Patent No.: US 9,212,999 B2  
(45) Date of Patent: Dec. 15, 2015

(54) DEVICE FOR DETERMINING THE CONCENTRATION OF AT LEAST ONE GAS IN A SAMPLE GAS STREAM

(71) Applicant: AVL EMISSION TEST SYSTEMS GMBH, Neuss (DE)

(72) Inventor: Norbert Kreft, Meerbusch (DE)

(73) Assignee: AVL EMISSION TEST SYSTEMS GMBH, Neuss (DE)

( * ) Notice: Subject to any disclaimer, the term of this patent is extended or adjusted under 35 U.S.C. 154(b) by 0 days.

(21) Appl. No.: 14/396,388

(22) PCT Filed: Mar. 12, 2013

(86) PCT No.: PCT/EP2013/054977  
§ 371 (c)(1),  
(2) Date: Oct. 23, 2014

(87) PCT Pub. No.: WO2013/159986  
PCT Pub. Date: Oct. 31, 2013

(65) Prior Publication Data  
US 2015/0125345 A1    May 7, 2015

(30) Foreign Application Priority Data  
Apr. 25, 2012   (DE) .......................... 10 2012 103 628

(51) Int. Cl.  
*G01N 21/76* (2006.01)  
*G01N 33/00* (2006.01)

(52) U.S. Cl.  
CPC .......... *G01N 21/766* (2013.01); *G01N 33/0037* (2013.01); *G01N 2201/0636* (2013.01); *G01N 2201/084* (2013.01); *G01N 2201/0806* (2013.01); *G01N 2201/0846* (2013.01)

(58) Field of Classification Search  
CPC ........................................................ G01N 21/76  
USPC ........................ 422/52, 82.07, 82.08; 385/12  
See application file for complete search history.

(56) References Cited

U.S. PATENT DOCUMENTS 4,130,758 A  * 12/1978  van Heusden ....... G01N 21/766  
                                                 250/361 C  
5,371,350 A     12/1994  Motolese  
(Continued)

FOREIGN PATENT DOCUMENTS

CH          696 085 A5     12/2006  
DE        27 16 284 A1    11/1977  
(Continued)

OTHER PUBLICATIONS

X. Yu et al.: "Chemiluminescence detection in liquid-core microstructured optical fibers", Sensors and Actuators B, vol. 160, pp. 800-803 (2011).

(Continued)

*Primary Examiner* — Jill Warden  
*Assistant Examiner* — Jacqueline Brazin  
(74) *Attorney, Agent, or Firm* — Norman B. Thot

(57) ABSTRACT

A device for determining a concentration of at least one gas in a sample gas stream includes an analysis chamber, a detector, and a connecting channel. The analysis chamber is configured to have the sample gas stream and a reaction gas stream be introduced therein. The sample gas stream and the reaction gas stream are mixed to a gas mixture which reacts so as to emit an optical radiation. The detector is configured to measure the optical radiation. The connecting channel is configured to connect the analysis chamber to the detector. The connecting channel is configured as a light conductor extending from the analysis chamber to the detector.

15 Claims, 1 Drawing Sheet

(56) References Cited

U.S. PATENT DOCUMENTS

| | | | |
|---|---|---|---|
| 5,714,121 A * | 2/1998 | Alderete | G01N 21/643 422/82.07 |
| 6,043,895 A * | 3/2000 | Masterson et al. | 356/436 |
| 6,176,962 B1 | 1/2001 | Soane et al. | |
| 6,882,418 B1 | 4/2005 | Bargende | |
| 7,008,594 B2 * | 3/2006 | Suzuki et al. | 422/52 |
| 2003/0161572 A1 | 8/2003 | Johnck et al. | |
| 2004/0252307 A1 * | 12/2004 | Arno | G01N 21/78 356/437 |
| 2006/0128196 A1 * | 6/2006 | McKinnon | 439/201 |

FOREIGN PATENT DOCUMENTS

| | | |
|---|---|---|
| DE | 100 29 946 A1 | 12/2001 |
| DE | 10 2004 015 906 A1 | 11/2005 |
| EP | 1 292 822 A1 | 3/2003 |
| GB | 2 016 679 A | 9/1979 |
| JP | 2-116768 A | 5/1990 |
| JP | 4-105088 A | 4/1992 |
| WO | WO 98/45693 A1 | 10/1998 |

OTHER PUBLICATIONS

K. S. Lok et al.: "Double spiral detection channel for on-chip chemiluminescence detection", Sensors and Actuators B, vol. 169, pp. 144-150 (2012).

X. Xie et al.: "Flow-injection determination of ethanol by fiber-optic chemiluminescence measurement", Analytica Chimica Acta, vol. 266, pp. 325-329 (1992).

M. V. Cattaneo et al.: "On-line chemiluminescence assay using FIA and fiber optics for urinary and blood glucose", Enzyme Microb. Technol., vol. 15, pp. 424-428 (1993).

M. V. Cattaneo et al.: "A chemiluminescence fiber-optic biosensor system for the determination of glutamine in mammalian cell cultures", Biosensors & Bioelectronics, vol. 7, pp. 569-574 (1992).

M. Hashimoto et al.: "Chemiluminescence detection of heme proteins separated by capillary isoelectric focusing", Journal of Chromatography A, vol. 852, pp. 597-601 (1999).

M. Hashimoto et al.: "Compact detection cell using optical fiber for sensitization and simplification of capillary electrophoresis-chemiluminescence detection", Journal of Chromatography A, vol. 832, pp. 191-202 (1999).

M. Magrisso et al.: "Fiber-optic biosensor to assess circulating phagocyte activity by chemiluminescence", Biosensors and Bioelectronics, vol. 21, pp. 1210-1218 (2006).

A. Chandrasekaran et al.: "Integrated biophotonic µTAS for flow cytometry and particle detection", Proceedings of SPIE, edited by Real Vallee, Conference Photonics North, vol. 7386., pp. 738603-1-738603-8 (2009).

* cited by examiner

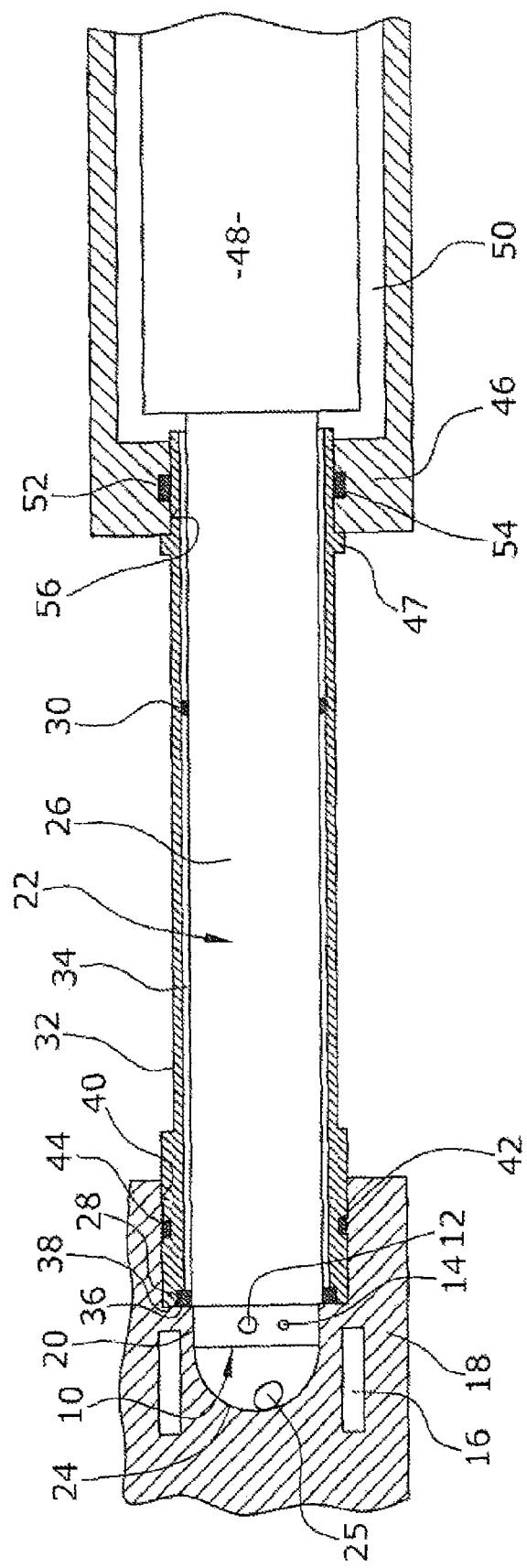

DEVICE FOR DETERMINING THE CONCENTRATION OF AT LEAST ONE GAS IN A SAMPLE GAS STREAM

CROSS REFERENCE TO PRIOR APPLICATIONS

This application is a U.S. National Phase application under 35 U.S.C. §371 of International Application No. PCT/EP2013/054977, filed on Mar. 12, 2013 and which claims benefit to German Patent Application No. 10 2012 103 628.4, filed on Apr. 25, 2012. The International Application was published in German on Oct. 31, 2013 as WO 2013/159986 A1 under PCT Article 21(2).

FIELD

The present invention relates to a device for determining the concentration of at least one gas in a sample gas stream, having an analysis chamber into which the sample gas stream and a reaction gas stream can be introduced, a detector which measures the optical radiation emitted by the reaction, and a connecting channel via which the analysis chamber is connected to the detector.

BACKGROUND

Such devices are known from the field of gas chromatography or chemiluminescence analysis and are used, for example, to determine the content of nitrogen monoxide in exhaust gases.

Oxygen and nitrogen dioxide are formed during the spontaneous reaction of nitrogen monoxide and ozone, with a part of the nitrogen dioxide produced being in an excited electron state. The molecules spontaneously emit this excessive energy in the form of optically measureable fluorescent radiation that is proportional to the concentration of nitrogen monoxide in the sample gas.

Since the reaction described applies only to the nitrogen monoxide molecules, the nitrogen dioxide parts in the exhaust gas are reduced to nitrogen monoxide before entering the analysis chamber. This is effected in a thermal or thermal/catalytic converter at temperatures above 200° C. Ozone for the reaction is further produced from oxygen in an ozonisator. The volume flow of the exhaust gas is maintained constant in order to achieve a light yield that is proportional to the nitrogen oxide concentration. The exhaust gas is correspondingly conducted into the analysis chamber via capillaries, the pressure and the temperature of the exhaust gas being controlled. The radiation is converted into an electric signal by means of a cooled photomultiplier that serves as a detector. This signal is supplied to the evaluation unit as a measure of the nitrogen oxide emission.

It has been found that particularly good results are achieved, for example, when high temperatures of above 100° C. are generated in the analysis chamber and cool temperatures prevail in the area of the detector. Moreover, due to diffusion or absorption, losses often occur during the measurement of the optical radiation.

DE-OS 27 16 284 describes a device for determining gaseous components in which a heated reaction chamber is provided which has an inlet for ozone and an inlet for the sample gas. The chamber is thermally separated by an asbestos ring from a photoelectric measuring cell arranged in a cooled housing. Two cylinders coated with a reflective material are arranged between the reaction chamber and the measuring cell, and two quartz glass windows mounted in a ring are arranged between the cylinders.

This device has the disadvantage that no full thermal separation is achieved with the two quartz glass windows. Radiation losses further occur due to absorption at the quartz glass windows since these are arranged in a ring. It is also doubtable whether the coating of the cylinders which is constantly exposed to the gas flow will, over the long term, fulfill its task of possibly providing a total reflection. Deposits of ammonia on the walls of the analysis chamber cannot be prevented.

SUMMARY

An aspect of the present invention is to provide a device for determining the concentration of at least one gas in a sample gas flow with which the analysis chamber can be operated at elevated temperatures to avoid ammonia or isocyanic acid deposits on the walls of the analysis chamber, and where the optical radiation produced by the reaction is made available to the detector as completely as possible for measurement so as to obtain measuring results that are as exact as possible.

In an embodiment, the present invention provides a device for determining a concentration of at least one gas in a sample gas stream which includes an analysis chamber, a detector, and a connecting channel. The analysis chamber is configured to have the sample gas stream and a reaction gas stream be introduced therein. The sample gas stream and the reaction gas stream are mixed to a gas mixture which reacts so as to emit an optical radiation. The detector is configured to measure the optical radiation. The connecting channel is configured to connect the analysis chamber to the detector. The connecting channel is configured as a light conductor extending from the analysis chamber to the detector.

BRIEF DESCRIPTION OF THE DRAWING

The present invention is described in greater detail below on the basis of embodiments and of the drawings in which:

FIG. 1 schematically shows a side elevational view of a device according to the present invention in the form of a chemiluminescence analyzer illustrated in section.

DETAILED DESCRIPTION

Because the connecting channel is configured as a light conductor that extends from the analysis chamber to the detector, losses in the measured light yield are minimized and a thermal separation of the analysis chamber and the detector is achieved via the light conductor so that the analysis chamber can be operated at an elevated temperature.

In an embodiment of the present invention, the light conductor can, for example, have a refractivity that differs from that of the environment, whereby a total reflection is achieved inside the light conductor.

A reflection of the emitted radiation is achieved due to the fact that the boundary surface of the light conductor is reflective. This can be achieved with a reflecting layer on the outer side of a glass rod or with a coating on the inner surface of an outer sleeve.

In an embodiment of the present invention, the light conductor can, for example, be surrounded by a sleeve. This facilitates the assembly of the light conductor and provides protection thereto at the same time.

In an embodiment of the present invention, a circumferential air gap is formed between the sleeve and the light conductor. A total reflection accordingly occurs at the boundary surface between the two transparent media glass and air so that the radiation generated in the analysis chamber is made almost completely available to the detector without having to provide for reflectivity.

The diameter of the light conductor is larger than the diameter of the analysis chamber in order to avoid diffusion losses and to provide that all of the emitted light enters the light conductor. This difference in diameter also prevents the light conductor from slipping towards the analysis chamber.

In an embodiment of the present invention, the light conductor can, for example, be supported in the sleeve with interposition of two seals. The contact surface of the light conductor is thus maintained small to the outer side so that only small surfaces are formed from where light can escape, i.e., where it is absorbed and is not reflected completely.

For a good support over the entire length of the light conductor, the first seal is arranged at the ends of the sleeve and the light conductor facing towards the analysis chamber, whereby the incidence of light into this region is reduced due to the larger diameter of the light conductor relative to the analysis chamber so that the losses during measurement are reduced.

A particularly simple assembly is achieved if the first seal is arranged in an annular recess in the inner circumference of the end of the sleeve facing towards the analysis chamber.

In an embodiment of the present invention, the seals can, for example, be white. The absorption of light waves is thereby further reduced when compared with black seals, whereby losses during measurement are reduced even further since the number of reflected waves is significantly higher.

A good light transmissivity of the light conductor is obtained if the light conductor is made from quartz glass that includes no chemical impurities.

For an increase in thermal separation of the two chambers, the length of the sleeve and of the light conductor is a multiple of the diameter of the analysis chamber.

In an embodiment of the present invention, the sleeve, with interposition of a sealing ring, protrudes into a receiving opening of a housing in which the analysis chamber is arranged. A sufficient tightness of the chamber is provided in this manner relative to the environment, while the assembly of the sleeve to the housing or to the analysis chamber is simple.

A tight fastening and a simple mounting of the sleeve to the detector is obtained in a similar manner if the sleeve, with interposition of a sealing ring, protrudes into a receiving opening of a housing in which the detector is arranged.

In an embodiment of the present invention, the device can, for example, comprise means for heating the analysis chamber, whereby the activation of the chemical reaction is significantly stronger so that the content of reacting nitrogen monoxide, and thus of nitrogen monoxide with an excited electron state, increases, whereby the accuracy of the measuring results can be improved significantly.

It can also be advantageous if the device includes means for cooling the detector since a reduction of dark current, and thus of signal noise, can be obtained at lower temperatures.

In an embodiment of the present invention, the analysis chamber can, for example, substantially have the shape of a hemisphere with an adjoining ring, in the diameter of which the inlet opening for the sample gas flow and the inlet opening for the reaction gas flow are formed, wherein the outlet opening for the gas mixture flow is formed in the hemisphere on the same side, with respect to the axis of symmetry, as the inlet openings formed in the ring. A long dwell time of the sample gas in the analysis chamber is achieved due to this arrangement so that a complete reactive conversion of the nitrogen monoxide can be assumed.

A device for determining the concentration of a gas in a sample gas flow is accordingly provided with which the concentration can be determined with high accuracy since signal losses caused by a poor transmission or by absorption, as well as insufficient reaction control or disadvantageous measuring conditions, are avoided.

An embodiment of a device of the present invention for determining the concentration of at least one gas in a sample gas flow is illustrated in FIG. 1 and will be described hereinafter with reference to the illustrated chemiluminescence analyzer for determining a content of nitrogen monoxide in exhaust gas.

The device of the present invention for determining the concentration of at least one gas in a sample gas flow has an analysis chamber 10 which in the present example forms a reaction chamber into which a sample gas mixture in the form of exhaust gas is introduced via a first inlet opening 12, while ozone is introduced into the analysis chamber 10 via a second inlet opening 14, the ozone serving as reaction gas. The exhaust gas is heated beforehand in a converter (not illustrated) in order to convert the nitrogen dioxide content present in the exhaust gas into nitrogen monoxide. The ozone for introduction into the analysis chamber 10 is further produced from oxygen in an ozonisator (not illustrated). The analysis chamber itself is operated at temperatures significantly above 100° C. in order to increase efficiency by reducing losses. These temperatures are generated by means of heating rods arranged in a first housing 18 that also contains the analysis chamber 10, the rods serving as means 16 for heating.

The two inlet openings 12, 14 are formed in a ring 20 that delimits the analysis chamber 10 towards a connecting channel 22. On the opposite side of the ring 20, a hemisphere 24 is formed whose walls merge into the ring 20 and which has an outlet opening 25 for the gas mixture produced by the reaction.

According to the present invention, the connecting channel 22 is a light conductor 26 of quartz glass that is arranged in a metal sleeve 32 with interposition of two seals 28, 30, the conductor being held in place by the seals 28, 30, wherein the seals 28, 30 create a gap 34 between the light conductor and the surrounding sleeve 32, the gap 34 extending over the entire length and the entire circumference of the light conductor 26. The length of the light conductor 26 corresponds to approximately six times its diameter.

The first seal 28 is arranged in an annular recess 36 at the end of the sleeve 32 and simultaneously abuts against a stop 38 that axially delimits a receiving opening 40 for the sleeve 32 in the first housing 18.

The sleeve 32 also has a circumferential groove 42 in its outer circumference in which a first sealing ring 44 is arranged, by which a sealing is made between the surrounding housing 18 and the sleeve 32.

The ends of the sleeve 32 and of the light conductor 26 opposite the analysis chamber 10 protrude into a second housing 46 of a Peltier cooler that serves as a means 50 for cooling a detector 48 which is configured as a photomultiplier and is arranged in the housing 46 of the Peltier cooler. The intensity of the electromagnetic waves of the radiation generated in the analysis chamber 10 is measured by means of the photomultiplier. The temperature at the detector 48 is adjusted to about 20° C. by means of the Peltier cooler. Sealing is effected by a second sealing ring 52 which is arranged in a groove 54 in a receiving opening 56 in the second housing 46 and whose inner side abuts on the outer side of the sleeve 32 which is secured against displacement towards the detector 48 by means of a protrusion 47 abutting on the housing 46.

When a constant flow of exhaust gas, whose nitrogen dioxide content has been reduced to nitrogen monoxide, is introduced into the analysis chamber 10 via the inlet opening 12 and an ozone-containing reaction gas flow is supplied at the same time into the analysis chamber 10 via the second inlet opening 14, the ozone will react with the nitrogen monoxide to form nitrogen dioxide and oxygen, however, with a percentage of the nitrogen molecules being in an excited state. The molecules spontaneously give off this excessive energy as optically measurable fluorescent radiation in the analysis chamber 10. This spontaneous release will occur primarily in the analysis chamber 10 since the dwell time is chosen so that, due to the arrangement of the inlet openings 12, 14 relative to the outlet opening 25, that the sample gas flow first flows to the side of the analysis chamber 10 opposite the inlet openings and then flows in a curve along almost the entire inner surface of the hemisphere 24 to the outlet opening 25 so that the path to be covered and thus the dwell time is maximized with respect to the size of the analysis chamber 10.

According to the present invention, this radiation will arrive at the detector 48 through the light conductor 26. This light conductor 26 provides for a good insulation between the hot analysis chamber 10 and the cold detector 48 due to its very poor thermal conduction properties and provides for an optimized transmission of the radiation intensity since a total reflection is effected at the surface of the light conductor 26 due to the surrounding air gap 34, the total reflection providing that no radiation can escape along the light conductor 26 so that it cannot be absorbed. The entire radiation is thereby made available to the photomultiplier provided, serving as a detector 48, for measurement thereby, so that, after a correct calibration, the content of nitrogen oxides in the exhaust gas can be determined very exactly.

The efficiency is also improved by the fact that, owing to the good thermal insulation properties of the light conductor 26, a high temperature can be used in the analysis chamber 10. The high temperatures can primarily prevent deposits of ammonia on the walls of the analysis chamber 10 which is often contained in exhaust gas due to the use of modern exhaust gas after-treatment systems with a selective catalytic reaction. The light conductor 26 and the sleeve 32 also effect a complete separation of the detector 48 from the analysis chamber 10 as far as gas is concerned.

The present invention is not limited to the embodiment described herein, and various modifications are possible within the scope of protection of the present main claim. A light conductor can also be used for gas chromatographs and for measuring other components in the sample gas mixture. Other structural modifications are also conceivable. Reference should also be had to the appended claims.

What is claimed is:

1. A device for determining a concentration of at least one gas in a sample gas stream, the device comprising:
   an analysis chamber configured to have the sample gas stream and a reaction gas stream be introduced therein, the sample gas stream and the reaction gas stream being mixed to a gas mixture which reacts so as to emit an optical radiation;
   an analysis chamber housing comprising a receiving opening, the analysis chamber housing being configured to have the analysis chamber be arranged therein;
   a first sealing ring;
   a detector configured to measure the optical radiation;
   a connecting channel configured to directly connect the analysis chamber to the detector; and
   a sleeve surrounding the connecting channel;
   wherein, the connecting channel is configured as a solid light conductor having a distal and a proximal end extending from the analysis chamber to the detector;
   wherein, the sleeve is arranged so as to protrude into the receiving opening of the analysis chamber housing, and the first sealing ring is arranged so as to be interpositioned between the analysis chamber housing and the sleeve sealing the analysis chamber to the proximal end of the solid light conductor.

2. The device as recited in claim 1, wherein the light conductor comprises a light conductor diameter and the analysis chamber comprises an analysis chamber diameter, the light conductor diameter being larger than the analysis chamber diameter.

3. The device as recited in claim 1, wherein the light conductor is made from a quartz glass.

4. The device as recited in claim 1, wherein the light conductor comprises a refractivity which is different from a refractivity of an environment surrounding the device.

5. The device as recited in claim 1, wherein the light conductor comprises a boundary surface configured to be reflective.

6. The device as recited in claim 1, further comprising a circumferential gap arranged between the sleeve and the light conductor.

7. The device as recited in claim 1, further comprising at least two seals arranged between the light conductor and the sleeve, the at least two seals being configured to support the light conductor in the sleeve.

8. The device as recited in claim 7, wherein the at least two seals comprise a first seal, the first seal being arranged at an end of the sleeve and at an end of the light conductor which are directed towards the analysis chamber.

9. The device as recited in claim 8, wherein the sleeve comprises an annular recess arranged in an inner circumference of the end of the sleeve directed towards the analysis chamber, the first seal being arranged in the annular recess.

10. The device as recited in claim 7, wherein the at least two seals are white.

11. The device as recited in claim 1, wherein the sleeve comprises a sleeve length, the light conductor comprises a light conductor length, and the analysis chamber comprises an analysis chamber diameter, the sleeve length and the light conductor length being a multiple of the analysis chamber length.

12. The device as recited in claim 1, further comprising:
   a detector housing comprising a receiving opening, the detector housing being configured to have the detector be arranged therein; and
   a second sealing ring,
   wherein, the sleeve is arranged so as to protrude into the receiving opening of the detector housing, and the second sealing ring is arranged so as to be interpositioned between the detector housing and the sleeve sealing the detector to the distal end of the solid light conductor.

13. The device as recited in claim 1, further comprising a heating device configured to heat the analysis chamber.

14. The device as recited in claim 1, further comprising a cooling device configured to cool the detector.

15. The device as recited in claim 1, wherein the analysis chamber is configured so as to substantially have a shape of a hemisphere comprising an adjoining ring, the device further comprising:
   a sample gas inlet opening for the sample gas stream arranged on the adjoining ring;

a reaction gas inlet opening for the reaction gas stream arranged on the adjoining ring; and an outlet opening for a flow of the gas mixture arranged in the hemisphere on a same side, with respect to an axis of symmetry, as the sample gas inlet opening and the reaction gas inlet opening arranged on the adjoining ring.

\* \* \* \* \*